United States Patent
Verard

(10) Patent No.: US 11,690,676 B2
(45) Date of Patent: Jul. 4, 2023

(54) ASSISTING APPARATUS FOR ASSISTING A USER DURING AN INTERVENTIONAL PROCEDURE

(71) Applicant: KONINKLIJKE PHILIPS N.V., Eindhoven (NL)

(72) Inventor: Laurent Verard, Katonah, NY (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 1266 days.

(21) Appl. No.: 14/787,279

(22) PCT Filed: May 21, 2014

(86) PCT No.: PCT/EP2014/060376
§ 371 (c)(1),
(2) Date: Oct. 27, 2015

(87) PCT Pub. No.: WO2014/191262
PCT Pub. Date: Dec. 4, 2014

(65) Prior Publication Data
US 2016/0081760 A1 Mar. 24, 2016

(30) Foreign Application Priority Data
May 31, 2013 (EP) .................... 13169953

(51) Int. Cl.
*A61B 34/20* (2016.01)
*A61B 90/11* (2016.01)
(Continued)

(52) U.S. Cl.
CPC .............. *A61B 34/20* (2016.02); *A61B 34/10* (2016.02); *A61B 90/11* (2016.02); *A61B 2034/2061* (2016.02); *A61B 2090/364* (2016.02)

(58) Field of Classification Search
CPC ..... A61B 34/20; A61B 34/10; A61B 19/5244; A61B 19/201; A61B 2090/364; A61B 2034/2061
See application file for complete search history.

(56) References Cited

U.S. PATENT DOCUMENTS 5,190,045 A * 3/1993 Frazin ................. A61B 8/06
600/463
7,450,743 B2 11/2008 Sauer et al.
(Continued)

FOREIGN PATENT DOCUMENTS

CN 1561926 A 1/2005
CN 2748042 Y 12/2005
(Continued)

OTHER PUBLICATIONS

Peters 2006 Phys.Med.Biol. 51:R505-R540.*
(Continued)

*Primary Examiner* — Keith M Raymond
*Assistant Examiner* — Patrick M Mehl

(57) ABSTRACT

The invention relates to an assisting apparatus (2) for assisting a user in moving an insertion element (11) like a catheter to a target element within, for instance, a person (8). A target element representation representing the target element within the object in its three-dimensional position and three-dimensional orientation and with its size is generated based on a provided target element image. Moreover, a three-dimensional position of the insertion element is tracked, while the insertion element is moved to the target element, and the target element representation and the tracked position of the insertion element are displayed. The three-dimensional position and orientation of the target element relative to the actual position of the insertion element can therefore be shown to the user, while the insertion element is moved to the target element, which (Continued)

allows the user to more accurately and faster move the insertion element to the target element.

20 Claims, 7 Drawing Sheets

(51) Int. Cl.
*A61B 34/10* (2016.01)
*A61B 90/00* (2016.01)

(56) References Cited

U.S. PATENT DOCUMENTS

| | | | |
|---|---|---|---|
| 7,632,304 B2* | 12/2009 | Park | A61F 2/856 623/1.34 |
| 7,772,541 B2 | 8/2010 | Duncan et al. | |
| 8,332,013 B2 | 12/2012 | Strommer | |
| 9,320,564 B2 | 4/2016 | Avitall et al. | |
| 9,332,928 B2 | 5/2016 | Markowitz et al. | |
| 2004/0034297 A1 | 2/2004 | Darrow et al. | |
| 2005/0104951 A1 | 5/2005 | Mitsuyasu et al. | |
| 2005/0107688 A1* | 5/2005 | Strommer | A61B 5/0066 600/424 |
| 2006/0079745 A1 | 4/2006 | Viswanathan et al. | |
| 2007/0031019 A1* | 2/2007 | Lesage | G06T 7/60 382/131 |
| 2008/0275467 A1 | 11/2008 | Liao et al. | |
| 2009/0163800 A1* | 6/2009 | Xu | A61B 6/12 600/424 |
| 2010/0217117 A1* | 8/2010 | Glossop | A61B 8/4245 600/424 |
| 2011/0237936 A1* | 9/2011 | Kalpin | A61M 5/14276 600/424 |
| 2011/0261180 A1 | 10/2011 | Bzostek et al. | |
| 2012/0059249 A1* | 3/2012 | Verard | A61B 5/062 600/424 |
| 2014/0296704 A1 | 10/2014 | Delnda et al. | |

FOREIGN PATENT DOCUMENTS

| | | |
|---|---|---|
| WO | 0209611 A2 | 2/2002 |
| WO | 2008071014 A1 | 6/2008 |
| WO | 2009129475 A1 | 10/2009 |

OTHER PUBLICATIONS

Gao et al. 2012 Proc. 2012 IEEE International Conference on Mechatronics and Automation, p. 1393-1398 (Year: 2012).*

Bernades 2012 Ph.D. Thesis Electrical Engineering University of Brasil Campus Darcy Ribeiro, Brasil / Montpellier France, 128 pages (Year: 2012).*

* cited by examiner

ASSISTING APPARATUS FOR ASSISTING A USER DURING AN INTERVENTIONAL PROCEDURE

CROSS-REFERENCE TO PRIOR APPLICATIONS

This application is the U.S. National Phase application under 35 U.S.C. § 371 of International Application Serial No. PCT/EP2014/060376, filed on May 21, 2014, which claims the benefit of European Patent Application Serial No. 13169953.0, filed on May 31, 2013. These applications are hereby incorporated by reference herein.

FIELD OF THE INVENTION

The invention relates to an assisting apparatus, an assisting method and an assisting computer program for assisting a user in moving an insertion element to be inserted into an object to a target element within the object. The invention relates further to an interventional system for introducing an insertion element into an object comprising the assisting apparatus.

BACKGROUND OF THE INVENTION

WO 2008/071014 A1 discloses a method for computer assisted distal locking of intramedullary nails. A virtual geometric representation of a distal part of an intramedullary nail with a distal locking hole is established, and first and second medical images are acquired by a radioscopic unit, wherein both images show the distal part with the distal locking hole and wherein the images have been acquired in different acquisition directions. The position of a longitudinal axis of the distal part and the position of an axis of the distal locking hole are computed by using the images and the virtual geometric representation. The computed positional information is used by an external guide means for drilling a hole in a bone which is aligned with the distal locking hole.

US 2005/0107688 A1 discloses a system for delivering a stent to a selected position within a lumen of a body of a patient, wherein the stent is attached to a catheter. The system comprises a user interface for receiving a position input indicating the selected position and a medical positioning system for determining the current position of the stent within the lumen. A processor superimposes a stent representation representing the current position of the stent, while the catheter is moved within the lumen, and a marking representation representing the position input on an image of the lumen.

US 2011/0261180 A1 discloses a system for performing a medical procedure on a patient, wherein the system comprises an imaging head defining a field of view relative to the patient. The imaging head includes a radio-frequency transmitter that emits a signal in the field of view and a radio-frequency receiver that receives a reflected signal based on an electrical property of a material in the field of view. A control module determines, based on the reflected signal received by the radio-frequency receiver, a location of a boundary of the material within the field of view, which is shown on a display.

Generally during minimally invasive interventions x-ray projection images are acquired and displayed for allowing a physician to determine the position of an insertion element like a guide wire and the position of a target element like a vessel opening within a person. The projection image is a two-dimensional image, which does not provide sufficient information for allowing the physician to accurately determine the positions of the insertion element and the target element within the person. The physician has therefore to, for instance, acquire projection images in different acquisition directions for more accurately determining these positions. This leads to a relatively high radiation dose applied to the person and takes a relatively long time.

SUMMARY OF THE INVENTION

It is an object of the present invention to provide an assisting apparatus, an assisting method and an assisting computer program for assisting a user in moving an insertion element to be inserted into an object to a target element within the object, which allow the user to move the insertion element to the target element within the object more accurately and faster. A target element is any part, component, piece, constituent, etc. of any object, and an insertion element is any item, tool, instrument, device, etc. insertable into the object and positionable to the target element.

In a first aspect of the present invention an assisting apparatus for assisting a user in moving an insertion element to be inserted into an object to a target element within the object is presented, wherein the assisting apparatus comprises:

a target element image providing unit for providing a target element image showing the target element, a target element representation generating unit for generating a target element representation representing the target element within the object in its three-dimensional position and three-dimensional orientation and with its size based on the target element image, wherein the target element comprises at least one opening, wherein the target element representation generating unit is adapted to generate a target element representation comprising at least one ring representing the at least opening of the target element within the object in the three-dimensional position, the three-dimensional orientation and size of the at least opening of the target element, a tracking unit for tracking a three-dimensional position of the insertion element within the object, while the insertion element is moved to the target element, wherein the tracked insertion element has at least one opening, and a display for displaying the at least one ring of the target element representation and at least one ring representing the at least one opening of the insertion element.

Since the target element representation is generated such that it represents the target element within the object in its three-dimensional position and three-dimensional orientation and with its size based on the target element image, wherein the tracking unit tracks the three-dimensional position of the insertion element within the object, while the insertion element is moved to the target element, and wherein the display displays this target element representation and the tracked position of the insertion element, the three-dimensional position and orientation of the target element relative to the actual position of the insertion element is provided to the user, while the insertion element is moved to the target element, which allows the user to more accurately and faster move the insertion element to the target element.

The tracking unit is preferentially adapted to track the three-dimensional position of the insertion element in real-time within the object, while the insertion element is moved to the target element. The display is preferentially adapted to display the target element representation representing the target element within the object in its three-dimensional position and three-dimensional orientation and with its size on a two-dimensional surface. For instance, the display can be adapted to simulate a projection of the target element representation onto the two-dimensional surface for displaying the target element representation on the two-dimensional surface. Also the three-dimensional position of the insertion element may be virtually projected onto the two-dimensional surface, in order to show the spatial relation between the target element and the insertion element on the display, especially in realtime.

The target element image providing unit can be adapted to provide a three-dimensional computed tomography image, magnetic resonance image, nuclear image like a positron emission tomography image or a single photon emission computed tomography image, an ultrasound image, et cetera as the target element image. However, the target element image providing unit can also be adapted to provide two or more two-dimensional images, in particular, two or more two-dimensional projection images, as target element images, wherein the target element representation generating unit can be adapted to generate the target element representation based on the two or more two-dimensional target element images. The object is preferentially a living being like a person or an animal, wherein the target element is preferentially an inner part of the living being like a vessel, especially an opening of a vessel. The insertion element may be an interventional device like a needle or a catheter. The insertion element can also be another interventional element like a graft, for instance, a stent.

The target element image providing unit can be a storing unit, in which the target element image is stored already and from which the target element image can be retrieved for providing the same. The target element image providing unit can also be a receiving unit for receiving the target element image from another unit like an imaging modality generating the target element image. Moreover, the target element image providing unit can be the imaging modality generating the target element image.

The target element representation generating unit is preferentially adapted to segment the target element within the provided target element image for generating the target element representation. The target element representation generating unit can be adapted to segment the entire target element or only a part of the target element for generating a target element representation. For instance, if the target element comprises an opening, the target element representation generating unit can be adapted to segment the edge of the opening only and to provide a ring-like target element representation having a three-dimensional position, a three-dimensional orientation and a size, which correspond to the three-dimensional position, the three-dimensional orientation and the size of the segmented opening. In an embodiment one or several target element images show the ostium of the renal artery and a ring may be sized, positioned and oriented such that it corresponds to the ostium of the renal artery, in order to generate the target element representation. The shape of the ring therefore depends on the shape of the opening. For instance, the ring may be elliptical, circular or shaped in another way. This displaying of the ring and the tracked position of the insertion element very effectively assists the user in moving the insertion element through the opening of the target element by moving the insertion element such that the displayed tracked position of the insertion element penetrates the displayed ring. The target element representation generating unit may also be adapted to generate a target element representation comprising an indication indicating a center of a ring having a three-dimensional position, a three-dimensional orientation and size which correspond to a three-dimensional position, a three-dimensional orientation and size of an opening of the target element.

The assisting apparatus may further comprise a projected position determination unit for determining the position of at least a part of the insertion element projected onto a ring plane defined by a ring of the target element representation, wherein the display is adapted to display the projected position of at least the part of the insertion element within the ring plane together with the ring. For example, the position of a tip of the insertion element may be projected onto the ring plane. This shows to the user how centrally the insertion element is actually arranged with respect to the opening of the target element, which allows the user to correct the position of the insertion element relative to the opening of the target element, for instance, by moving the insertion element within the object such that the projected position of the insertion element displayed on the display is located more centrally within the displayed ring. If a part of the insertion element is already located within the ring, the position of this part may be regarded as the projected position such that it can be indicated how centrally this part is located within the ring.

The target element comprises preferentially a tube-like element, wherein the target element representation generating unit is adapted to generate a target element representation comprising a cylinder having a three-dimensional position, a three-dimensional orientation and size which correspond to a three-dimensional position, a three-dimensional orientation and size of the tube-like element of the target element. This allows providing information also about the length of the target element or of a part of the target element to the user, which may further improve the assisting of the user in positioning the insertion element relative to the target element.

In an embodiment the target element comprises several openings, wherein the target element representation generating unit is adapted to generate a target element representation comprising several rings representing the several openings of the target element within the object in the three-dimensional position, the three-dimensional orientation and size of the openings of the target element, wherein also the tracked insertion element has openings and wherein the display is adapted to display the rings of the target element representation and rings representing the openings of the insertion element. The user therefore just needs to move the insertion element such that on the display the rings representing the openings of the insertion element match the rings of the target element representation, in order to accurately position the insertion element within the target element. In this example the insertion element is preferentially a stent having openings, which should be positioned within a vessel, which also has openings, such that the openings of the stent match the openings of the vessel.

The assisting apparatus may further comprise a distance determination unit for determining a distance between the target element and the insertion element based on the generated target element representation and the tracked position of the insertion element, wherein the display is adapted to display the determined distance. Moreover, the tracking unit may be adapted to also track an orientation of the insertion element within the object, wherein the assisting apparatus may further comprise an orientation determination unit for determining an orientation of the insertion element relative to the target element based on the generated target element representation and the tracked orientation of the insertion element, wherein the display is adapted to display the determined orientation. Displaying the distance of the insertion element relative to the target element and/or the orientation of the insertion element relative to the target element provides further information to the user, which may allow the user to position the insertion element relative to the target element even faster and/or even more accurately.

In a preferred embodiment the assisting apparatus comprises an object image providing unit for providing an object image showing at least a part of the object, wherein the display is adapted to display the target element representation and the tracked position of the insertion element on the object image, i.e. the display may be adapted to display the target element representation in its three-dimensional position and orientation and with its size on the object image. In particular, the object image providing unit may be adapted to provide a pre-acquired image and/or an actual image of the object as the object image. In an embodiment the tracked position is the position of the tip of the insertion element. It may be displayed as a simplified icon on the object image, which may be a two-dimensional realtime image like a two-dimensional x-ray fluoroscopy image.

The object image providing unit may be adapted to provide several object images, which correspond to different image acquisition directions, wherein the display may be adapted to display the target element representation and the tracked position of the insertion element on the several object images. For instance, the object image providing unit may be adapted to provide several, particularly two, two-dimensional object images, wherein the display may be adapted to display the target element representation and the tracked position of the insertion element on the several two-dimensional object images. If two object images are provided, they preferentially correspond to acquisition directions which are perpendicular to each other. Displaying the target element representation and the tracked position of the insertion element on an object image provides the user with further helpful information, particularly anatomical information if the object image is an anatomical image, which can allow the user to position the insertion element relative to the target element even faster and even more accurately.

In an embodiment the tracking unit is adapted to also track the orientation of the insertion element, wherein the object image providing unit is adapted to provide the object image such that its image acquisition direction depends on the tracked orientation of the insertion element. For instance, the object image providing unit can comprise assignments between orientations of the insertion element relative to the target element and acquisition directions, wherein the object image providing unit can be adapted to select the image acquisition direction for providing the object image based on the actual tracked orientation of the insertion element relative to the target element and the stored assignments. These assignments can be predefined such that always an object image is displayed in an image acquisition direction, which is optimized for assisting the user in positioning the insertion element relative to the target element.

The object image providing unit and the target element image providing unit can be integrated, i.e. the same unit can provide the target element image and the object image. Moreover, the object image can be the target element image, i.e. the target element representation can be generated based on the object image and the target element representation can then be shown together with the tracked position of the insertion element on the object image.

In an embodiment the target element image providing unit is adapted to provide a live image of the target element as the target element image, the target element representation generating unit is adapted to generate a live target element representation representing the target element within the object in its actual three-dimensional position and three-dimensional orientation and with its size based on the live target element image, and the display is adapted to display the live target element representation and the tracked position of the insertion element. This allows the user to fast and accurately approach the target element, even if the target element moves during the insertion procedure.

The assisting apparatus may further comprise a moving zone providing unit for providing a zone within the object, within which the insertion element should be moved only, wherein the display is adapted to also display the moving zone. The moving zone providing unit can be adapted to provide a stored moving zone, which has been determined before inserting the insertion element, or the moving zone providing unit can be adapted to determine the moving zone. The moving zone can be regarded as being a safety zone, in which the insertion element should be moved only. For instance, the moving zone can be ring-like or tubular, for example, cylindrical or forming a curvilinear tube, wherein the moving zone may be arranged within a vessel and dimensioned such that, if the insertion element remains within the moving zone, inner walls of the vessel are not touched by the insertion element. The moving zone can be determined by segmenting elements within the object in an object image and/or in a target element image and by defining a forbidden region around the segmented elements, which should not be entered by the insertion element. The moving zone can help the user to avoid, for instance, dissections.

The tracking unit is preferentially adapted to track the position of the insertion element by using optical shape sensing. For instance, optical shape sensing can be used to provide a four-dimensional tracking of the insertion element, while the insertion element is moved to the target element. This tracking can be performed in a way which is relatively simple for the user. For instance, no further external fields like electromagnetic fields, no further radiation like further x-ray radiation, et cetera is needed for tracking the position of the insertion element within the object.

In a further aspect of the present invention an interventional system for introducing an insertion element into an object is presented, wherein the interventional system comprises the insertion element and the assisting apparatus as defined in claim 1.

In a further aspect of the present invention an assisting method for assisting a user in moving an insertion element within an object to a target element is presented, wherein the assisting method comprises:

providing a target element image showing the target element by a target element image providing unit, generating a target element representation representing the target element within the object in the three-dimensional position, the three-dimensional orientation and the size of the target element based on the target element image by a target element representation generating unit, wherein the target element comprises at least one opening, wherein the target element representation generating unit generates a target element representation comprising at least one ring representing the at least one opening of the target element within the object in the three-dimensional position, the three-dimensional orientation and size of the at least one opening of the target element, tracking a three-dimensional position of the insertion element within the object by a tracking unit, while the insertion element is moved to the target element, wherein the tracked insertion element has at least one opening, and displaying the at least one ring of the target element representation and at least one ring representing the at least one opening of the insertion element by a display.

In another aspect of the present invention an assisting computer program for assisting a user in moving an insertion element within an object to a target element is presented, wherein the assisting computer program comprises program code means for causing an assisting apparatus as defined in claim 1 to carry out the steps of the assisting method as defined in claim 13, when the assisting computer program is run on a computer controlling the assisting apparatus.

It shall be understood that the assisting apparatus of claim 1, the interventional system of claim 12, the assisting method of claim 13 and the assisting computer program of claim 14 have similar and/or identical preferred embodiments, in particular, as defined in the dependent claims.

It shall be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION OF EMBODIMENTS

Figure 1:
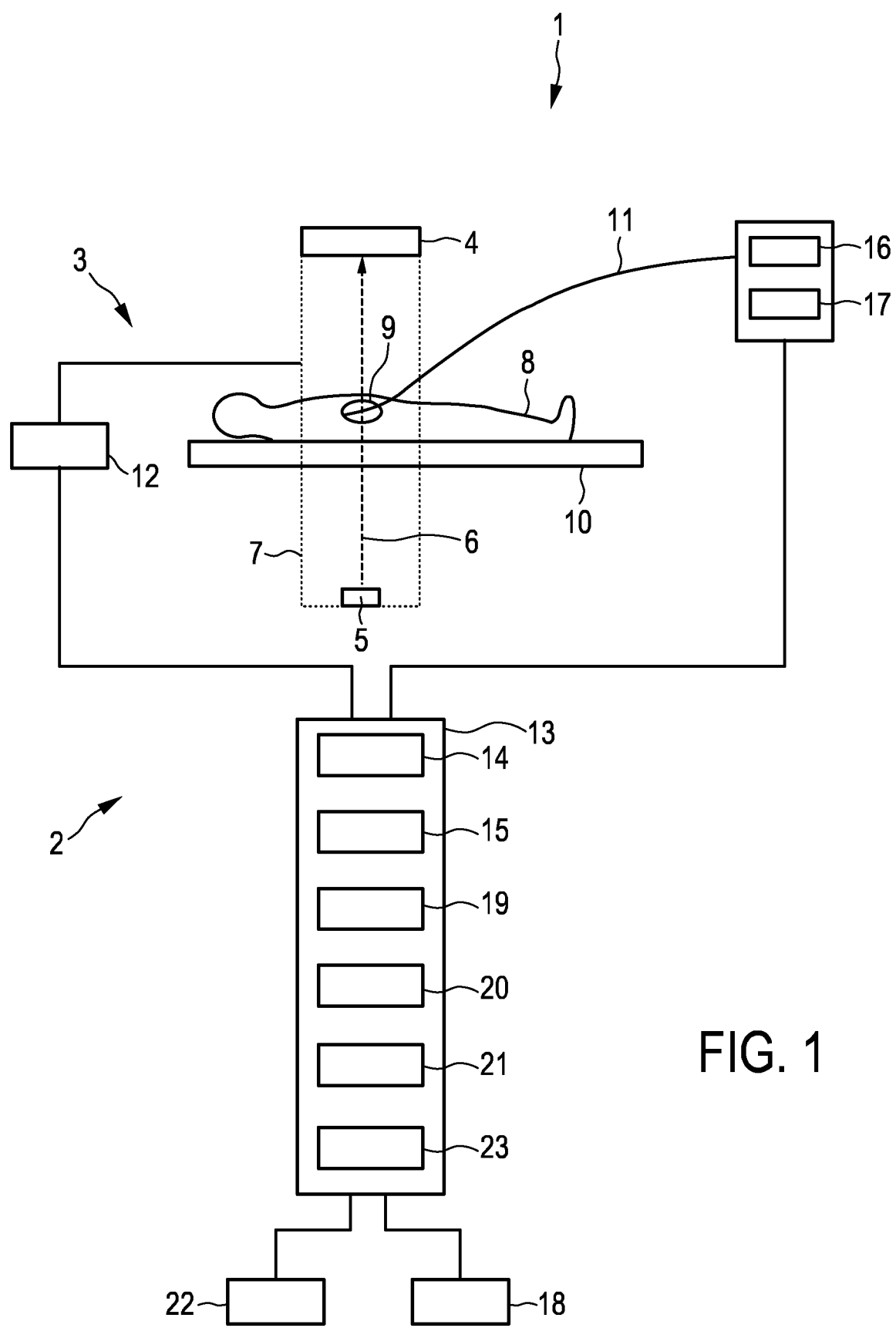
FIG. 1 shows schematically and exemplarily an embodiment of an interventional system for introducing an insertion element into a person.

FIG. 1 shows schematically and exemplarily an embodiment of an interventional system for introducing an insertion element into a person. In this embodiment the insertion element is catheter 11 to be inserted into a heart 9 of the person 8 lying on a support means 10 like a table. A user like a physician can navigate the catheter 11 within the person 8 by using a handling unit 16. The handling unit 16 may allow the user to directly manipulate the catheter 11 or to manipulate the catheter 11 via a joystick, a graphical user interface or another means.

The interventional system 1 comprises an assisting apparatus 2 for assisting the user in moving the catheter 11 to a target element within the person 8. The assisting apparatus 2 comprises a computing device 13 with a target element image providing unit 14 for providing a three-dimensional target element image showing the target element and a target element representation generating unit 15 for generating a target element representation representing the target element within the object in its three-dimensional position and three-dimensional orientation and with its size based on the target element image. In this embodiment the target element image providing unit 14 is a storing unit, in which a three-dimensional computed tomography image showing the target element is stored as the three-dimensional target element image, and the target element representation generating unit 15 is adapted to generate the target element representation by segmenting the target element in the provided three-dimensional computed tomography image.

The assisting apparatus 2 further comprises a tracking unit 17 for tracking the position of the insertion element 11 within the person 8. In this embodiment the tracking unit 17 is adapted to track the position of the insertion element 11 by using optical shape sensing. Thus, the insertion element 11 comprises an optical fiber being adapted to allow the tracking unit 17 to determine the position of the insertion element 11 within the person 8 by optical shape sensing. The optical shape sensing may be performed in accordance with the description in U.S. Pat. No. 7,772,541 B2, or in accordance with another known optical shape sensing technique.

The assisting apparatus 2 further comprises an object image providing unit 3 for providing an object image being, in this embodiment, an actual image of at least a part of the person 8 including the target element. Object image providing unit 3 is any type of imaging modality, particularly for interventional procedures. In this embodiment the object image providing unit 3 is a C-arm fluoroscopy device comprising an x-ray tube 5 for emitting x-rays 6 for traversing the person 8. The fluoroscopy device 3 further comprises an x-ray detector 4 for detecting the x-rays 6 after having traversed the person 8. The x-ray tube 5 and the x-ray detector 4 are mounted on a C-arm 7, which is movable with respect to the support means 10 and thus with respect to the person 8, in order to allow the object image providing unit 3 to acquire actual projection images in different acquisition directions. The C-arm 7, the x-ray tube 5 and the x-ray detector 4 are controlled by a control unit 12, which is also adapted to produce the actual images based on detection values received from the x-ray detector 4. The produced actual images are two-dimensional projection images.

The assisting apparatus 2 further comprises an input unit 22 for allowing the user to input commands like a start command for starting the assisting procedure or a stop command for stopping the assisting procedure and a display 18. The input unit 22 may be a keyboard, a computer mouse, a touch screen, et cetera. The display 18 is adapted to display the target element representation and the tracked position of the insertion element 11 on the acquired actual image, i.e. in this embodiment on the acquired two-dimensional x-ray fluoroscopy projection image.

In an embodiment the target element comprises a tube-like element and an opening, i.e. the target element is a tube-like element with an opening or the target element is a larger component comprising besides other elements the tube-like element and an opening, wherein the opening may be an opening of the tube-like element or an opening of another element of the target element. For example, the target element may comprise a vessel with an opening. The target element representation generating unit 15 can then be adapted to generate a target element representation comprising a ring having a three-dimensional position, a three-dimensional rotation and size, which correspond to a three-dimensional position, a three-dimensional rotation and size of the opening. For instance, the target element may comprise the ostium of the renal artery and the target element representation generating unit 15 may be adapted to generate a ring sized, positioned and oriented such that it corresponds to the ostium of the renal artery. The target element representation generating unit 15 may also be adapted to generate a target element representation comprising a cylinder having a three-dimensional position, three-dimensional orientation and size, which correspond to a three-dimensional position, three-dimensional orientation and size of the tube-like element of the target element. Moreover, the target element representation generating unit 15 may be adapted to generate a target element representation comprising an indication indicating a center of a ring having a three-dimensional position, three-dimensional orientation and size, which correspond to a three-dimensional position, three-dimensional orientation and size of an opening of the target element.

The target element may also comprise several openings, wherein in this case the target element representation generating unit 15 may be adapted to generate a target element representation comprising several rings representing the several openings of the target element within the person 8 in the three-dimensional position, the three-dimensional orientation and the size of the openings of the target element.

The display 18 is adapted to display the respective target element representation and the respective tracked position of the insertion element on the respective actual image of the person 8. On the actual image at least the target element representation is displayed such that this displaying of the target element representation corresponds to the three-dimensional position, three-dimensional orientation and the size of the target element representation, in order to allow the user to grasp this three-dimensional information from the displaying of the target element representation on the actual image. This displaying is performed such that the user can see the three-dimensional position, the three-dimensional orientation and the size of the target element representation relative to the insertion element on the actual image being the object image in this example. For instance, the display 18 can be adapted to virtually project the determined target element representation onto the object image under consideration of the image acquisition geometry used for generating the object image. Also the tracked three-dimensional position of the insertion element can be projected onto the two-dimensional object image in this way, in order to visualize the three-dimensional spatial relation between the target element and the insertion element on the object image.

The displaying of the target element representation and of the tracked position of the insertion element on the respective actual image will be illustrated further below with reference to FIGS. 2, 6, 11 and 13.

Figure 2:
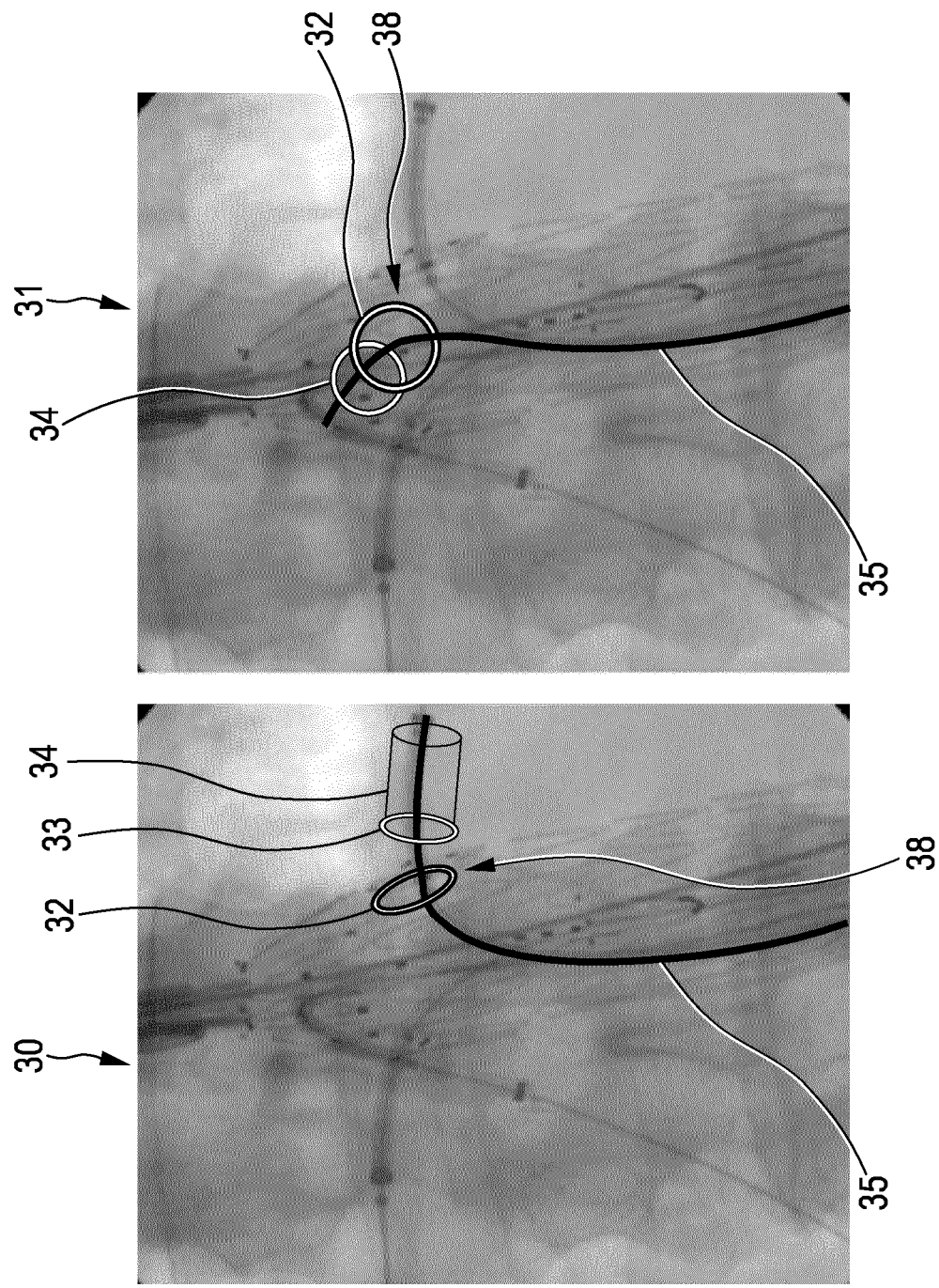
FIG. 2 shows schematically and exemplarily two object images with representations of a target element and of an insertion element to be shown on a display of the interventional system.

The object image providing unit 3 can be adapted to acquire two-dimensional object images in at least two image acquisition directions, which may be perpendicular to each other. Such two object images 30, 31 are exemplarily and schematically shown in FIG. 2. In FIG. 2 the target element representation 38 comprises two rings 32, 33 and a cylinder 34, wherein on the left object image 30 also the cylinder 34 is displayed and on the right object image 31 only the two rings 32, 34 are displayed, because the acquisition direction of the right object image 31 is parallel to the longitudinal axis of the cylinder 34. Also the tracked position of the insertion element as determined by optical shape sensing is indicated in the object images 30, 31 by the line 35. In this example the two object images 30, 31 can be pre-acquired object images, or one object image can be a pre-acquired object image and the other object image can be an actual live object image. The two object images 30, 31 together with the target element representation and the three-dimensional position of the insertion element can be regarded as forming a virtual biplane view, in which the position of the insertion element, in particular, the line 35, can be shown in a three-dimensional live view on both object images simultaneously together with the target element representation. In this virtual concept one monoplane projection system, i.e. the monoplane object image providing unit 3, can acquire, for instance, two projection images, wherein the view provided by the system can be similar to the view of a biplane system like a true physical biplane C-arm system.

Figure 3:
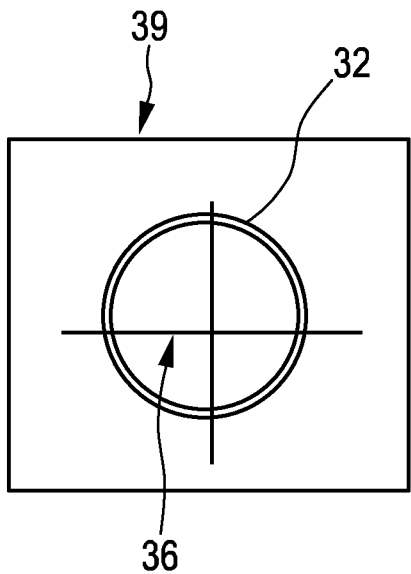
FIGS. 3 and 4 show schematically and exemplarily a position of a part of an insertion element relative to a ring of a target element representation.
Figure 4:
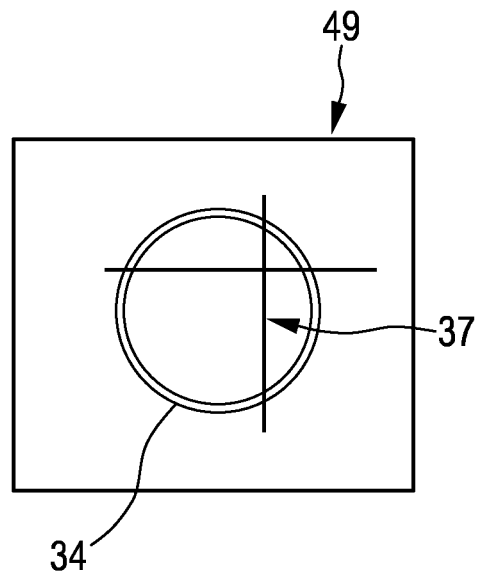

The assisting apparatus 2 further comprises a projected position determination unit 19 for determining the position of the insertion element projected onto a ring plane defined by the respective ring 32, 34, wherein the display 18 is adapted to also display the projected position of the insertion element within the ring plane 39, 49 together with the ring 32, 34 as schematically and exemplarily illustrated in FIGS. 3 and 4. In these figures the projected position is indicated by the crosses 36 and 37, respectively. If the tip of the insertion element has not already passed the respective ring 32, 34, the projected position of the insertion element is preferentially the projected position of the tip of the insertion element. If the tip of the insertion element has already passed the respective ring 32, 34 as schematically and exemplarily shown in FIG. 2, the projected position shown in FIGS. 3 and 4 by the crosses 36, 37 are the positions of the respective part of the insertion element in the respective ring plane 39, 49 as determined by optical shape sensing. The crosses 36, 37 can be regarded as being crosshairs, which further assist the user in navigating the insertion element through the target element.

Figure 5:
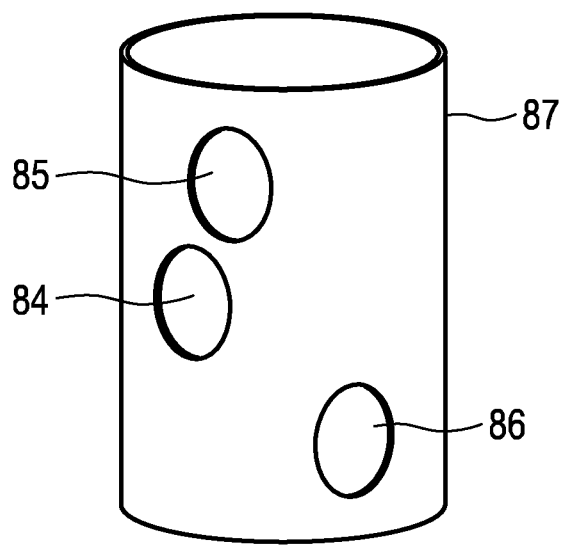
FIG. 5 shows schematically and exemplarily an embodiment of an insertion element.
Figure 6:
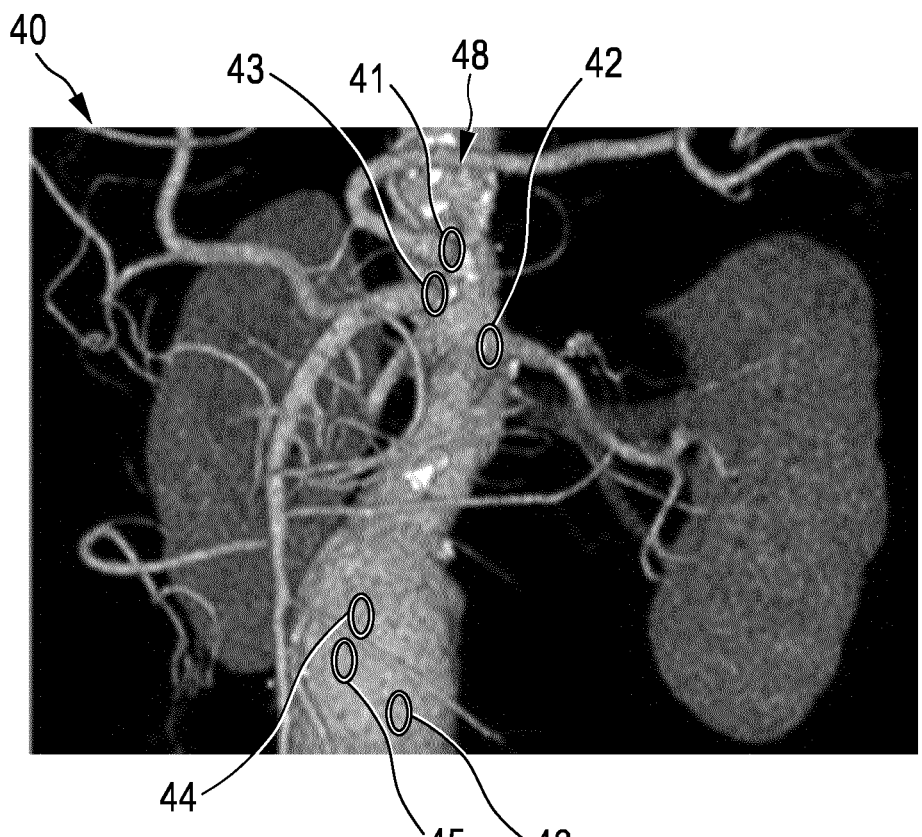
FIG. 6 shows schematically and exemplarily an object image with representations of a target element and an insertion element to be shown on the display of the interventional system.

In an embodiment the target element may be a vessel having several side openings and the insertion element may be a stent having corresponding side openings, wherein the stent should be positioned within the vessel by using, for instance, the catheter 11 such that the openings of the stent match the openings of the vessel. FIG. 5 schematically and exemplarily illustrates such a stent 87 with openings 84, 85 and 86. FIG. 6 schematically and exemplarily shows a target element representation 48 with three rings 41, 42, 43 representing the three openings of the vessel and three rings 44, 45, 46 indicating the position of the openings of the stent as determined by optical shape sensing on an object image 40. In particular, the dimensions of the openings 84, 85 and 86 of the stent 87 and the orientations and positions of these openings 84, 85 and 86 relative to the stent 87 can be determined from x-ray projection images showing the stent 87, which may be provided by the object image providing unit 3, i.e. by the above described x-ray C-arm system. In particular, features of the openings of the stent can be manually or automatically extracted from two or more x-ray projection images, which correspond to different image acquisition directions and which show the stent 87 with the openings 84, 85 and 86, wherein these extracted features can be used to determine the size and the three-dimensional position and orientation of the rings 84, 85 and 86 relative to the three-dimensional position and orientation of the stent 87 such that based on these spatial relations and the tracked three-dimensional position and three-dimensional orientation of the stent 87 the three-dimensional position and three-dimensional orientation of the rings 84, 85 and 86 can be determined. For instance, the extracted features may be markers around the respective opening, which may be extracted, particularly automatically extracted, by using a stent boost algorithm as for example described in WO2005104951A1, wherein these markers may then be used to determine the dimensions, and the orientations and positions of the openings 84, 85 and 86 relative to the three-dimensional position and orientation of the stent. The resulting three-dimensional representation of these rings 84, 85 and 86 can be shown on the display 18. When the user moves the stent within the person, the rings 44, 45, 46 are moved accordingly on the display 18 as determined by optical shape sensing such that the user can correctly position the stent 87, if the user moves the stent such that the rings 44, 45, 46 match the rings 41, 42, 43 on the display 18.

Figure 7:
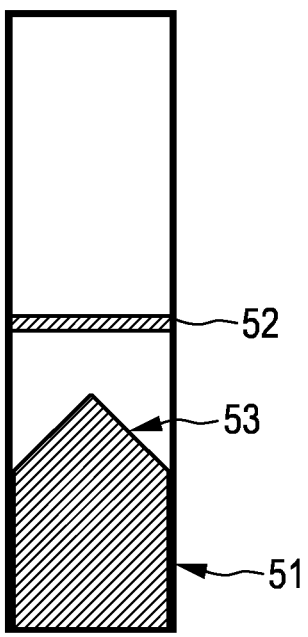
FIGS. 7 and 8 show schematically and exemplarily indications indicating distances between the target element and the insertion element to be shown on the display of the interventional system.
Figure 8:
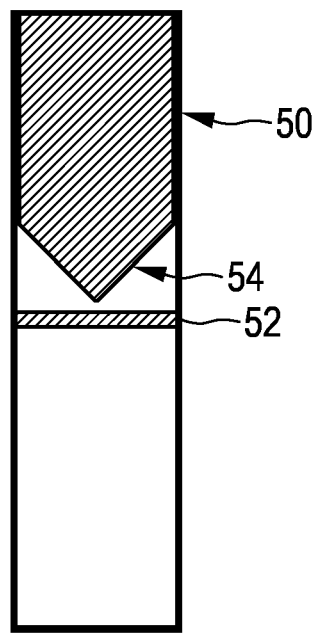

The assisting apparatus 2 further comprises a distance determination unit 20 for determining a distance between the target element and the insertion element based on the generated target element representation 48 and the tracked position of the insertion element 87, wherein the display 18 is adapted to display also the determined distance. This is illustrated in FIGS. 7 and 8. In FIG. 7 a line 52 is shown, which symbolizes the zero distance between the desired position of the stent 87 and the actual position of the stent 87 and the bar 51 with the tip 53 indicates the distance to the desired final position of the stent and the required movement direction of the stent. In this example the tip 53 of the bar 51 indicates a forward movement direction. If the stent 87 has been moved too far, this may be indicated as schematically and exemplarily shown in FIG. 8, in which the tip 54 of the bar 50 points in a direction being opposite to the direction in which the tip 53 of the bar 51 points in FIG. 7. In addition to illustrating the distance to the final desired position of the stent 87 as shown in FIGS. 7 and 8, the distance may also explicitly be displayed on the display 18, i.e. it may be displayed that the distance between the actual position of the stent 87 and the desired final position of the stent 87 is, for example, +2 mm or −3 mm.

Figure 9:
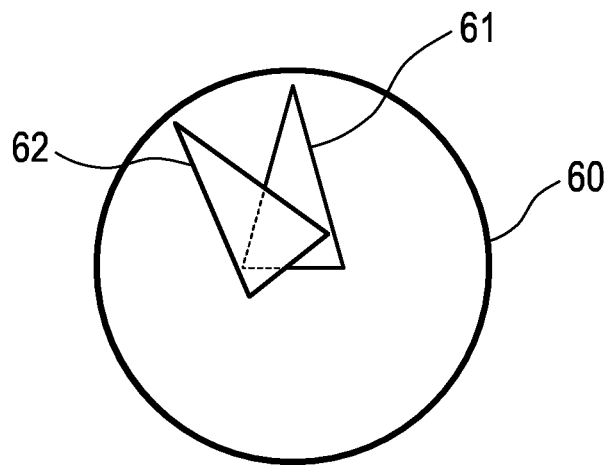
FIG. 9 shows schematically and exemplarily an indication for indicating an orientation of the insertion element relative to the target element to be shown on the display of the interventional system.

The tracking unit 17 is preferentially also adapted to track the orientation of the insertion element within the person 8 and the assisting apparatus 2 preferentially further comprises an orientation determination unit 21 for determining an orientation of the insertion element relative to the target element based on the generated target element representation and the tracked orientation of the insertion element, wherein the display 18 may be adapted to display also the determined orientation. For instance, with reference to FIGS. 5 and 6 the orientation determination unit 21 may determine the orientation of the openings 84, 85, 86 of the stent 87 in a circumferential direction of the stent 87 relative to the positions of the openings 41, 42, 43 of the target element representation 48. This orientation may be indicated on the display 18 as schematically and exemplarily shown in FIG. 9. In FIG. 9 the triangle 61 within the circle 60 indicates the correct desired rotational position of the stent and the triangle 62 indicates the actual rotational position of the stent, i.e. the actual rotational position of the openings 44, 45, 46 in the circumferential direction of the stent 87. If the user modifies this rotational position of the stent 87, this will directly be shown by a corresponding rotational movement of the triangle 62. In this way the user can rotate the stent 87 such that its rotational position matches the final desired rotational position by using the display of the rotational positions as illustrated in FIG. 9.

Thus, the user can start pushing the endograft 87 represented by the virtual rings 44, 45 and 46 in the positions schematically and exemplarily shown in FIG. 6, in order to slowly shift the endograft 87 to the position and the orientation schematically and exemplarily indicated by the rings 41, 42 and 43 in FIG. 6, which represent the desired final position and orientation of the endograft 87. If the rings 44, 45 and 46 match the rings 41, 42 and 43, this indicates to the user that the original endograft openings 84, 85, 86 match the vessel ostia. It should be noted that FIG. 6 is just a schematic figure for illustrating the concept of displaying the target element representation 48 and the tracked position 44, 45, 46 of the insertion element, which is an endograft in this example, i.e., for instance, in a real application the rings may have a different size.

In an embodiment, when the stent approaches the target element as observable by optical shape sensing tracking, which may also be named optical shape sensing imaging, translation and rotation parameters may alternatively or additionally be obtained by using a single value decomposition algorithm, wherein the position of the stent tracked by optical shape sensing can be used as an initialization or as a constraint of the solution space of the single value decomposition algorithm. The single value decomposition algorithm, which may be performed by the distance determination unit and/or the orientation determination unit, may be applied to a first set of points defining the positions of the openings of the vessel, in particular, defining positions of landmarks around the openings of the vessel, which may be obtained from the target element image, and to a second set of points defining the positions of the openings of the stent, in particular, defining positions of landmarks around the openings of the stent, which may be obtained from live images like live x-ray projection images. The result of this application of the single value decomposition algorithm is a 4×4 matrix that provides translation and rotation information, which is indicative of the remaining translation and rotation of the stent required for generating a best match between the openings of the vessel and the openings of the stent. This remaining translation and rotation may be calculated and shown on the display in real-time, particularly as illustrated in FIGS. 7 to 9.

In FIG. 6 the provided object image is a three-dimensional segmented vessel image. However, in other embodiments the object image, on which the target element representation and the tracked position, for instance, corresponding rings, are displayed, can be another kind of image like a real two-dimensional projection image, a two-dimensional cross section of a three-dimensional computed tomography image, a virtual two-dimensional projection image determined by virtually forward projecting an image of the object which may be a model of the object, et cetera. Moreover, the object image may be an image, which has been acquired before the interventional procedure or during the interventional procedure. Furthermore, the target element and the tracked position, i.e., for instance, corresponding rings, may be displayed simultaneously on several object images like different two-dimensional projection images which correspond to different image acquisition directions.

The assisting apparatus 2 further comprises a moving zone providing unit 23 for providing a zone within the object, within which the insertion element should be moved only, wherein the display 18 is adapted to also display the moving zone. In this embodiment the moving zone is a safety zone, wherein the insertion element should be navigated such that it remains within the safety zone. The moving zone providing unit 23 can be adapted to provide an already stored moving zone or it can be adapted to determine the moving zone depending on, for instance, the target element image and/or the object image. In particular, an element visible in the target element image or the object image can be segmented and the moving zone can be determined such that the segmented element and a region around the segmented element are excluded from the moving zone. For example, the segmented element may be an inner vessel wall and the moving zone may be determined such that it is arranged within the vessel and with a distance to the inner vessel wall, in order to avoid a touching of the walls along the entire insertion element while being moved to the target element. This can reduce the likelihood of unwanted dissections.

Figure 10:
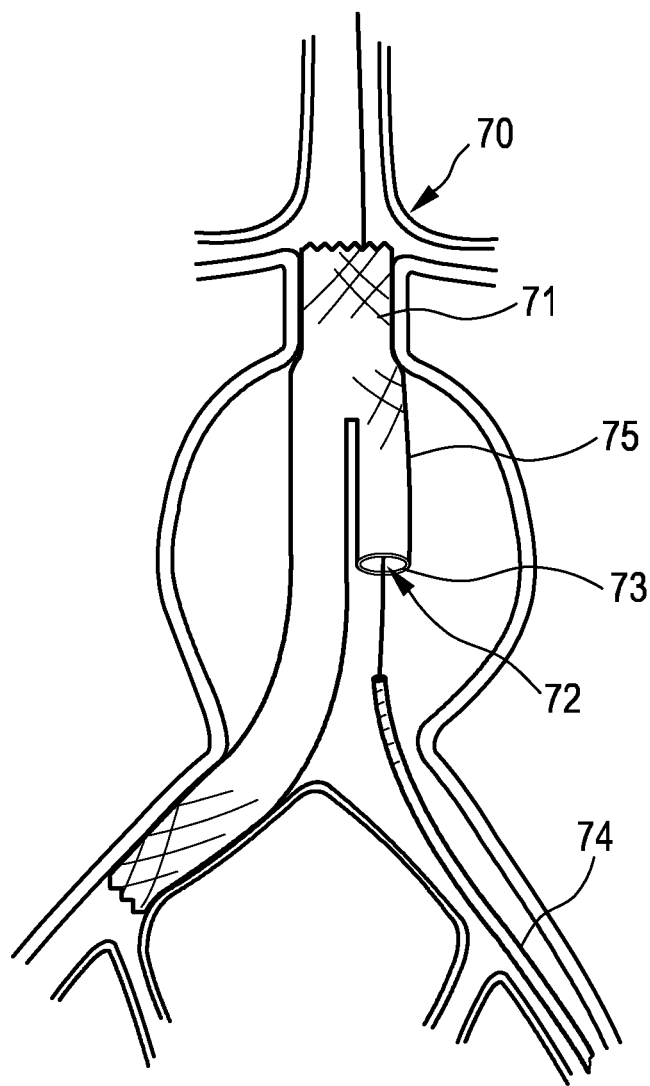
FIG. 10 illustrates schematically and exemplarily an endograft within a vessel structure, wherein the endograft is cannulated by using a catheter.
Figure 11:
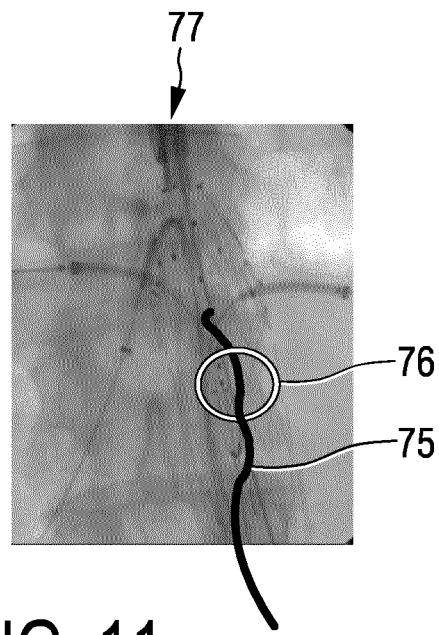
FIG. 11 shows schematically and exemplarily an object image with representations of a target element and an insertion element to be shown on the display of the interventional system.
Figure 12:
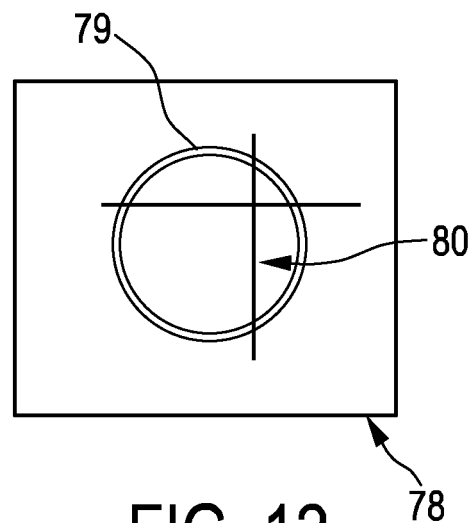
FIG. 12 shows schematically and exemplarily an indication for indicating the position of the insertion element relative to a ring of the target element to be shown in the display of the interventional system.

FIG. 10 schematically and exemplarily illustrates a cannulation of a contra-lateral limb of an endograft 71 within a vessel structure 70. In this example the target element 73 is the ring surrounding the opening 72 of the limb 75 of the endograft 71. FIG. 11 shows schematically and exemplarily a target element representation 76 being a ring displayed on an actual image 77 in its three-dimensional position, three-dimensional orientation and its size, which correspond to the three-dimensional position, the three-dimensional orientation and the size of the ring 73 surrounding the opening of the limb 75 of the endograft 71. Also a line 75 indicating the catheter 74 is shown on the actual image 77. FIG. 12 shows the position of a part of the catheter 74 intersecting a ring plane 78 defined by the ring 73, wherein in FIG. 12 the ring is indicated by the circle 79 and the position of the part of the catheter 74 within the ring 73 is indicated by the cross 80.

The x-ray C-arm system 3 can be adapted to provide object images corresponding to different acquisition directions, particularly to perpendicular acquisition directions. For instance, it can be adapted to provide a left anterior oblique image, a right anterior oblique image, a cranial image and/or a caudal image of, for example, a target vessel. If the target element is a target vessel, the x-ray C-arm system 3 can also be adapted to provide a cross-section view object image showing the target vessel. For acquiring the cross-section view object image showing the target vessel the C-arm is moved in an orientation that is "bull's eye" of the tube formed by the target vessel, wherein the image acquisition direction is substantially aligned with the axis of the target vessel.

The tracking unit 17 is preferentially also adapted to track the orientation of the insertion element, wherein the object image providing unit 3, i.e. in this embodiment the x-ray C-arm system 3, is adapted to provide the object image such that its acquisition direction depends on the tracked orientation of the insertion element.

If the target element representation comprises several elements like the two rings 32, 33 shown in FIG. 2, the object image providing unit 2 can be adapted such that, if the insertion element approaches the first ring 32, an object image is shown, which allows the user to accurately cannulate the first ring 32, and to display an object image, which allows the user to accurately cannulate the second ring 33, if the insertion element has traversed the first ring 32 and approaches the second ring 33. For instance, if the insertion element approaches the first ring 32, the object image providing unit 3 can provide an object image having an acquisition direction being substantially perpendicular to the ring plane defined by the first ring 32 and, if the insertion element approaches the second ring 33, the object image providing unit 3 may show an object image having an acquisition direction being substantially perpendicular to the ring plane defined by the second ring 33. Thus, the C-arm can follow the optical shape sensing device orientation to best cannulate the first ring 32 and then automatically reposition the angulation to optimize for a best cannulation of the second ring 33, i.e. the C-arm and the target elements can be sync'ed via optical shape sensing in space and time. The dependence of the respective acquisition direction on the respective optical shape sensing orientation can be predefined, in particular, predefined by the user in accordance with the user's preferences. For instance, the dependence may be predefined such that the acquisition direction encloses with the respective ring plane an angle of, for example, 45°.

The object image providing unit 3 may be adapted to provide a single two-dimensional fluoroscopy image, a cine two-dimensional fluoroscopy image, two two-dimensional fluoroscopy images for providing a biplane view, more than two two-dimensional fluoroscopy images et cetera. However, the object image providing unit may also be adapted to provide an actual three-dimensional image, in particular, a live three-dimensional image, which may be provided by an ultrasound imaging unit. Moreover, instead of providing an actual image, also an older image may be shown for providing anatomical context, wherein on this older image the target element representation and an indication indicating the insertion element may be shown. Furthermore, the anatomical context can also be provided in another way. For instance, a roadmap can be displayed together with the target element representation and a representation of the insertion element for providing the anatomical context. The roadmap may be determined in advance by segmenting a vessel structure in a three-dimensional image of the person, which may be a computed tomography image or a magnetic resonance image.

Although in the embodiment described above with reference to FIG. 1 the object image providing unit is adapted to provide an x-ray fluoroscopy image of the person 8, which preferentially includes the insertion element, in particular, the tip of the insertion element, the object image providing unit may also be adapted to use another imaging modality for providing the actual image like an ultrasound imaging unit.

The object image providing unit can be adapted to provide an actual image of a part of the person only, which includes the tracked position of the insertion element, particularly the tracked position of the tip of the insertion element. For example, collimators of the C-arm fluoroscopy system described above with reference to FIG. 1 can be adapted to focus the x-rays 6 onto a region within the person including the tracked position of the insertion element. This focusing of the radiation onto this region can be performed automatically or manually given the respective tracked position of the insertion element. An automatic feedback loop can be implemented, in order to enable the object image providing unit to provide an actual image of the region including the insertion element based on the tracked position of the insertion element. This focusing of the radiation onto this region can reduce the x-ray radiation applied to the person. If in another embodiment instead of or in addition to the C-arm fluoroscopy system another imaging modality is used for providing an object image like a computed tomography system, a three-dimensional ultrasound system, a magnetic resonance imaging system et cetera, also to these imaging modalities the concept of focusing the imaging onto, for instance, a tip or any desired part of the optical shape sensing enabled insertion element can be applied.

Figure 13:
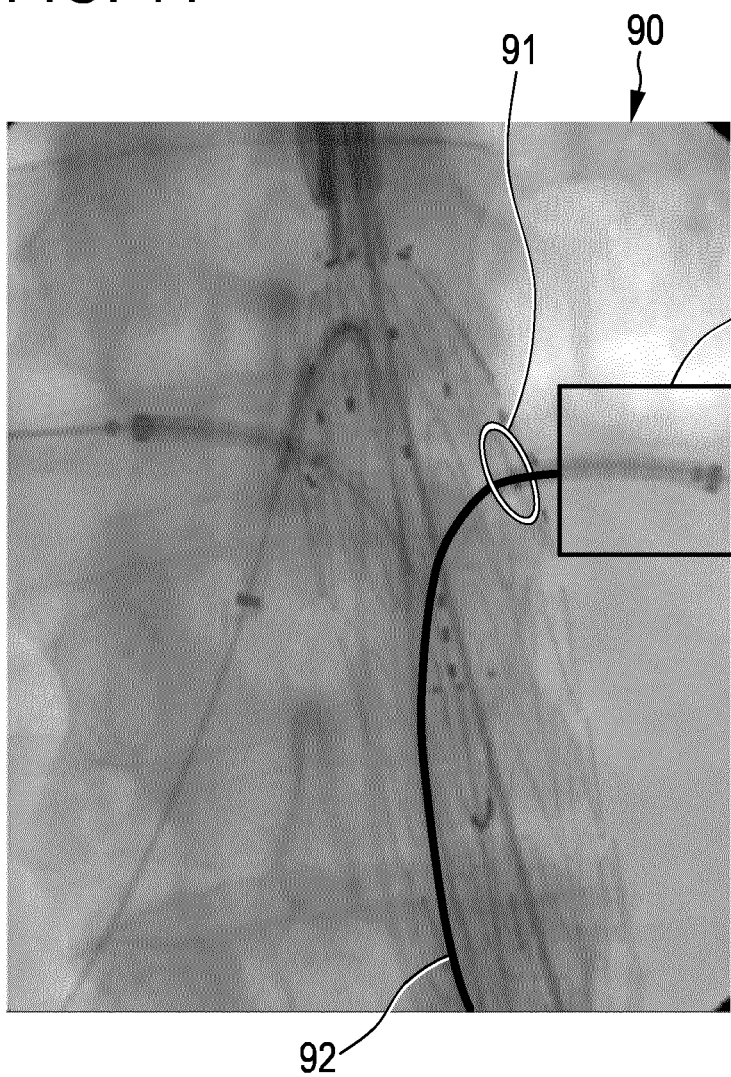
FIG. 13 shows schematically and exemplarily an object image with representations of a target element and of an insertion element and with a magnified view in which the tip of the insertion element is magnified.

In an embodiment the display is adapted to display a part of the actual image, which includes the tracked position of the insertion element, in particular, the tracked position of the tip of the insertion element, in a magnified view as schematically and exemplarily shown in FIG. 13. As can be seen in FIG. 13, a target element representation 91 and a line indicating the insertion element 92 can be displayed on an actual image 90, wherein the tip of the insertion element being, in this embodiment, a catheter, is shown in a magnified view 93.

Figure 14:
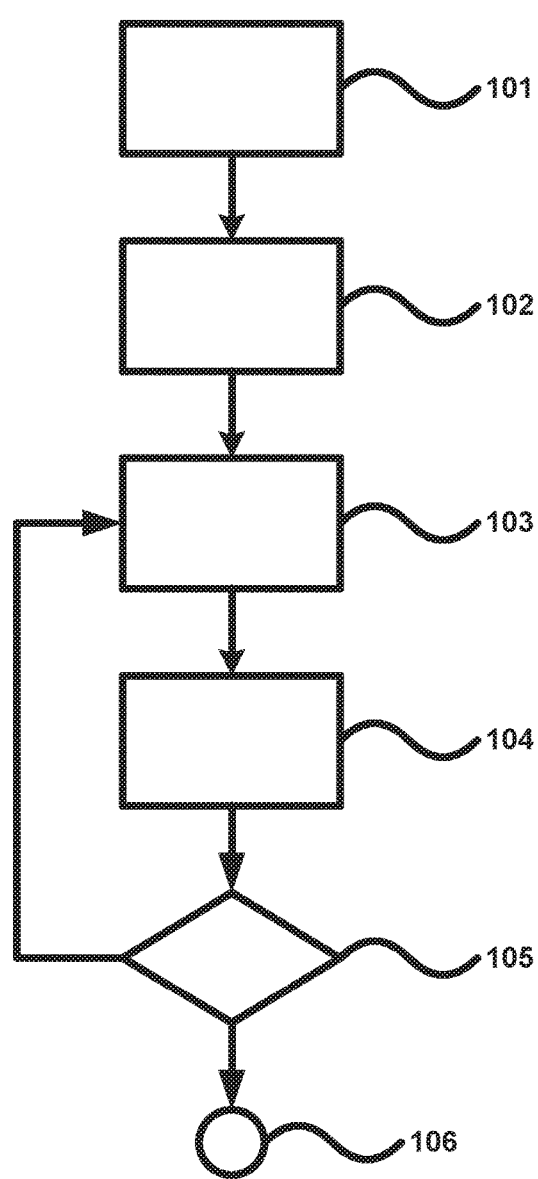
FIG. 14 shows a flowchart exemplarily illustrating an embodiment of an assisting method for assisting a user in moving an insertion element within a person to a target element.

In the following an embodiment of an assisting method for assisting a user in moving an insertion element within an object to a target element will exemplarily be described with reference to a flowchart shown in FIG. 14.

In step 101 a three-dimensional target element image is provided, which shows the target element, by the target element image providing unit 14. In step 102 a target element representation representing the target element within the object in the three-dimensional position, the three-dimensional orientation and the size of the target element is generated based on the target element image by the target element representation generating unit 15. In step 103 the tracking unit 17 tracks the position of the insertion element within the object and in step 104 the target element representation and the tracked position of the insertion element are shown by the display 18. In step 105 it is determined whether an abort criterion is fulfilled, wherein, if the abort criterion is not fulfilled, the assisting method continues with step 103. Otherwise the assisting method ends in step 106. The abort criterion may be, for instance, whether a user has input an abort command into the system by using the input unit 22 or whether the insertion element has reached the target element.

The system described above with reference to FIG. 1 can be adapted to position and probably size a three-dimensional ring on an image as the main target of the anatomy, i.e. as the target element. This main target of the anatomy may be, for instance, the ostium of the renal artery, which can be represented as a three-dimensional ring of, for instance, 8 mm diameter in a precise position and angulation at the ostium. The position and size can be obtained from a computed tomography scan of the patient, which may be provided as the target element image and which may be segmented. The target element image can be registered to the real-time image, i.e. to the actual object image, for instance, via fluoroscopy or optical shape sensing.

The target element image providing unit, the object image providing unit, i.e. in the above described embodiment the x-ray C-arm system, and the tracking unit are registered with respect to each other. The registration between these different components can be performed in several ways. For instance, if the target element image providing unit is adapted to provide a three-dimensional computed tomography image as the target element image and if the object image providing unit is adapted to provide two or more two-dimensional x-ray projection images as the object images, the target element image providing unit and the object image providing unit can be registered with respect to each other by performing a known 2D-3D registration. If the object image providing unit is adapted to provide an intra-interventional computed tomography image, the computed tomography target element image may be registered with the computed tomography object image by using, for instance, point matching or volume matching procedures. Moreover, the tracking unit can be registered with the object image providing unit by identifying the position of the insertion element in the object image and by also determining this position by the tracking unit. The tracking unit is then also registered with the target element image providing unit, if the target element image providing unit is registered with the object image providing unit. The tracking unit can also directly be registered with the target element image providing unit by, for instance, detecting the shape of certain vessels shown in the target element image and by matching these shapes with the tracked shape of the insertion element, when the insertion element is inserted into these vessels.

The assisting apparatus described above with reference to FIG. 1 provides the relevant and meaningful information to cannulate, for instance, the renal artery, as a simple three-dimensional ring on an interventional two-dimensional x-ray image. The tracked interventional device, i.e. the insertion element, is then approached to hit the target element, wherein a simplified "icon" live crosshair representation of the tracked interventional device can be displayed to meet the inside of the ring. The tracking of the interventional device is preferentially performed by means of optical shape sensing. The three-dimensional ring can be augmented as a cylinder to offer information about the length or depth of the targeted artery to optimize cannulation safety and properly assist with the sizing of, for instance, an angioplasty balloon or stent.

The assisting apparatus can further be adapted to enable a virtual biplane environment as the anatomy can be visualized with the imager, i.e. with the object image providing unit, from two or more perspectives, for instance, in a left anterior oblique and a right anterior oblique direction. The context of simple x-ray images can provide a context for the physician that he/she is used to. The indication of the interventional device and the one or several rings of the target element representation are preferentially overlaid in three dimensions and live in all viewing images, i.e. in all images used for providing the anatomical context. This renders a simple yet intuitive and powerful environment to help a physician to engage with the target, thereby reducing trials-and-errors, saving time and reducing unnecessary radiation and contrast.

The assisting apparatus described above with reference to FIG. 1 is preferentially adapted to be used during an endovascular aneurysm repair (EVAR) procedure.

The assisting apparatus can be adapted to determine several target element representations for several target elements and to allow the user to select one or several of the target element representations to be displayed on the display.

For instance, the assisting apparatus can be adapted to provide a pull-down menu for allowing the user to select a desired target element representation. This may allow the user to focus on a certain target element only, for instance, on the right renal artery, because only the target element representation determined for this respective target element may be shown on the display and not other target element representations determined for other target elements, i.e. the other target element representations may be hidden.

Although in above described embodiments the target element image providing unit is adapted to provide several two-dimensional target element images or a three-dimensional target element image, in other embodiments the target element image providing unit can also be adapted to provide a four-dimensional target element image, i.e. a dynamic three-dimensional target element image. For instance, the target element image providing unit can be adapted to provide cardiac and respiratory gated pre-acquired three-dimensional images as the four-dimensional target element image, or a live three-dimensional image as the target element image. In these cases the target element representation generating unit can be adapted to generate a dynamic target element representation, which can be shown on the display together with the tracked position of the insertion element optionally on an object image for providing some anatomical information. Also the object image providing unit can be adapted to provide a dynamic three-dimensional image.

Although in above described embodiments the target element image providing unit is adapted to provide one or several target element images of a same imaging modality, in another embodiment the target element image providing unit may be adapted to provide images from different imaging modalities or images from fused imaging modalities as target element images, wherein the target element representation generating unit can be adapted to generate the target element representation based on the target element images from different or fused imaging modalities. These different or fused imaging modalities may include at least two of x-ray projection imaging, computed tomography imaging, magnetic resonance imaging, ultrasound imaging, et cetera, wherein the respective image of the respective imaging modality may be a two-dimensional image, a three-dimensional image or a four-dimensional image. Also the object image providing unit can be adapted to provide several object images from different or fused imaging modalities, wherein the target element representation and the tracked position of the insertion element may be displayed on the several object images from the different or fused imaging modalities.

Although in above described embodiments the target element representation generating unit is adapted to generate a target element representation comprising a ring, in other embodiments the target element representation generating unit may be adapted to generate a target element representation comprising another element like a cube, a sphere, et cetera, which is dimensioned, oriented and positioned such that its dimension, orientation and position correspond to the dimension, orientation and position of the target element, which in this case has substantially the shape of a cube, a sphere, et cetera.

Although in an above described embodiment the insertion element is a stent having three openings, the insertion element can also be a stent having only a single opening, two openings or more than three openings. Moreover, the insertion element may also be another element, especially another element to be inserted having one or more openings.

In an embodiment a single ring of a target element representation may be displayed together with a single ring representing a single opening of an insertion element like a fenestrated stent.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Operations like the generation of the target element representation, the determination of the distance between the target element and the insertion element, the determination of the orientation of the insertion element relative to the target element et cetera performed by one or several units or devices, can be performed by any other number of units or devices. These operations and/or the control of the assisting apparatus in accordance with the assisting method can be implemented as program code of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Referring back to FIG. 1, computing device 13 may be implemented in various combinations of electronic components/circuitry, hardware, executable software and executable firmware, particularly as application modules of a controller as described herein, and provide functions which may be combined in a single element or multiple elements. For example, the functions of target element image providing unit 14, target element representation generating unit 15, tracking unit projected position determination unit 19, distance determination unit 20, orientation determination unit 21, and a moving zone providing unit 23 shown in FIG. 1 can be provided through the use of dedicated hardware as well as hardware capable of executing software in association with appropriate software.

Figure 15:
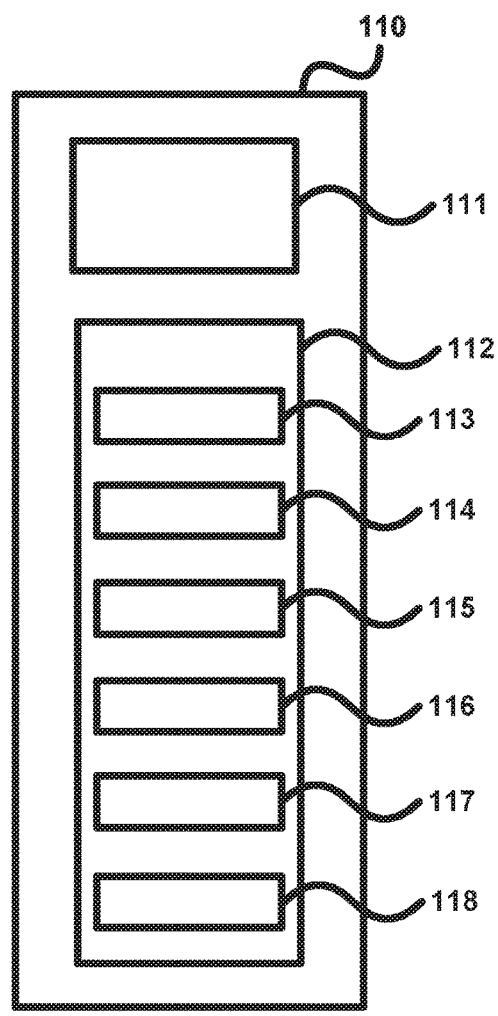
FIG. 15 shows schematically and exemplarily an embodiment of an computer device.

Referring to FIG. 15, an embodiment 110 of computing device 13 (FIG. 1) employs one or more processors 111 and one or more memories 112.

In practice, processor(s) 111 may be provided by a single dedicated processor, by a single shared processor, or by a plurality of individual processors, some of which can be shared and/or multiplexed. Moreover, explicit use of the term "processor" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, circuitry, combinations thereof, etc.) which is capable of (and/or configurable) to perform and/or control a process.

A target element image providing unit 113, a target element representation generating unit 114, a tracking unit projected position determination unit 115, a distance determination unit 116, an orientation determination 117, and a moving zone providing unit 118 are computer program products or application modules accessible from non-transitory memory(ies) 112 providing program code and/or instructions for use by or in connection with processor(s) 111. In practice, memory(ies) 112 may be electronic, magnetic, optical, electromagnetic, infrared or semiconductor system (or apparatus or device) or a propagation medium. Non-limiting examples of a memory(ies) 112 include, e.g., a semiconductor or solid state memory, magnetic tape, a removable computer diskette, a random access memory (RAM), a read-only memory (ROM), flash (drive), a rigid magnetic disk and an optical disk. Current examples of optical disks include compact disk—read only memory (CD-ROM), compact disk—read/write (CD-R/W) and DVD.

Any reference signs in the claims should not be construed as limiting the scope.

The invention relates to an assisting apparatus for assisting a user in moving an insertion element like a catheter to a target element within, for instance, a person. A target element representation representing the target element within the object in its three-dimensional position and three-dimensional orientation and with its size is generated based on a provided target element image. Moreover, a three-dimensional position of the insertion element is tracked, while the insertion element is moved to the target element, and the target element representation and the tracked position of the insertion element are displayed. The three-dimensional position and orientation of the target element relative to the actual position of the insertion element can therefore be shown to the user, while the insertion element is moved to the target element, which allows the user to more accurately and faster move the insertion element to the target element.

The invention claimed is:

1. An assisting apparatus for assisting a user in moving an insertion element to be inserted into an object to a target element within the object, the assisting apparatus comprising:
   a tangible, non-transitory computer readable medium that stores instructions, which when executed by a processor, causes the processor to:
   provide an object image showing at least a part of the object, wherein a target element within the object is invisible in the object image;
   generate a target element representation representing the target element within the object in a three-dimensional position of the target element and a three-dimensional orientation of the target element and with a size of the target element based on a target element image, wherein the target element includes at least one opening;
      generate the target element representation including at least one ring representing the at least opening of the target element within the object in the three-dimensional position, the three-dimensional orientation and size of the at least one opening of the target element; and
   track a three-dimensional position of the insertion element within the object, while the insertion element is moved to the target element, and generate at least one ring representing the at least one opening of the insertion element,
      wherein: the insertion element is invisible in the object image, and the tracked three-dimensional position of the insertion element has at least one opening; and
   a display for displaying the at least one ring of the target element representation and the at least one ring representing the at least one opening of the insertion element on the object image.

2. The assisting apparatus as defined in claim 1, wherein the instructions when executed by the processor, further cause the processor to:
   determine a position of at least a part of the insertion element projected onto a ring plane defined by a ring of the target element representation,
      wherein the display is adapted to display a projected position of at least the part of the insertion element within the ring plane together with the ring.

3. The assisting apparatus as defined in claim 1,
   wherein the target element comprises a tube-like element; and
   wherein the instructions, when executed by the processor, further cause the processor to generate a target element representation including a cylinder having a three-dimensional position, a three-dimensional orientation and size which correspond to a three-dimensional position, a three-dimensional orientation and size of the tube-like element of the target element.

4. The assisting apparatus as defined in claim 1,
   wherein the target element includes several openings;
   wherein the instructions, when executed by the processor, further cause the processor to generate a target element representation including several rings representing the several openings of the target element within the object in the three-dimensional position, the three-dimensional orientation and size of the openings of the target element;
   wherein the tracked three-dimensional position of the insertion element has openings; and
   wherein the display is adapted to display the rings of the target element representation and rings representing the openings of the insertion element.

5. The assisting apparatus as defined in claim 1,
   wherein the instructions, when executed by the processor, further cause the processor to determine a distance between the target element and the insertion element based on the generated target element representation and the tracked position of the insertion element,
      wherein the display is adapted to display the determined distance.

6. The assisting apparatus as defined in claim 1,
   wherein the instructions, when executed by the processor, further cause the processor to track an orientation of the insertion element within the object; and
   wherein the instructions, when executed by the processor, further cause the processor to determine an orientation of the insertion element relative to the target element based on the generated target element representation and the tracked orientation of the insertion element; and
   wherein the display is adapted to display the determined orientation.

7. The assisting apparatus as defined in claim 1,
   wherein the instructions, when executed by the processor, further cause the processor to provide a target element image showing the target element,
      wherein the display is adapted to display the at least one ring of the target element representation and the at least one ring representing the at least one opening of the insertion element on the target element image.

8. The assisting apparatus as defined in claim 1,
wherein the instructions, when executed by the processor, further cause the processor to track the orientation of the insertion element; and
wherein the instructions, when executed by the processor, further cause the processor to provide the object image such that an image acquisition direction of the object image depends on the tracked orientation of the insertion element.

9. The assisting apparatus as defined in claim 1,
wherein the instructions, when executed by the processor, further cause the processor to provide a live image of the object; and
wherein the instructions, when executed by the processor, further cause the processor to generate a live target element representation representing the target element within the object in an actual three-dimensional position of the live target element and a three-dimensional orientation of the live target element and with a size of the live target element based on a live target element image; and
wherein the display is adapted to display the live target element representation and the tracked position of the insertion element on the object image.

10. The assisting apparatus as defined in claim 1,
wherein the instructions, when executed by the processor, further cause the processor to provide a zone within the object, within which the insertion element should be moved only,
wherein the display is adapted to also display the moving zone.

11. The assisting apparatus as defined in claim 1, wherein the instructions, when executed by the processor, further cause the processor to track the position of the insertion element by using optical shape sensing.

12. An interventional system for introducing an insertion element into an object, the interventional system comprising:
the insertion element; and
the assisting apparatus as defined in claim 1.

13. An assisting method for assisting a user in moving an insertion element within an object to a target element, the assisting method executed by a processor, the method comprising:
providing an object image showing at least a part of the object by an object image providing unit, wherein a target element within the object is invisible in the object image;
generating a target element representation representing the target element within the object in a three-dimensional position, a three-dimensional orientation and a size of the target element based on a target element image, wherein the target element includes at least one opening, and
generating the target element representation including at least one ring representing the at least one opening of the target element within the object in the three-dimensional position, the three-dimensional orientation and size of the at least one opening of the target element;
tracking a three-dimensional position of the insertion element within the object while the insertion element is moved to the target element,
wherein the insertion element is invisible in the object image,
wherein the tracked insertion element has at least one opening;
generating at least one ring representing the at least one opening of the insertion element; and
displaying the at least one ring of the target element representation and at least one ring representing the at least one opening of the insertion element on the object image by a display.

14. The assisting method as defined in claim 13, the method further comprising:
determining a position of at least a part of the insertion element projected onto a ring plane defined by a ring of the target element representation; and
displaying a projected position of at least the part of the insertion element within the ring plane together with the ring.

15. The assisting method as claimed in claim 13, wherein the target element comprises a tube-like element, the method further comprises generating a target element representation including a cylinder having a three-dimensional position, a three-dimensional orientation and size which correspond to a three-dimensional position, a three-dimensional orientation and size of the tube-like element of the target element.

16. The assisting method as claimed in claim 13, wherein the target element includes several openings, and the method further comprises:
generating a target element representation including several rings representing the several openings of the target element within the object in the three-dimensional position, the three-dimensional orientation and size of the openings of the target element, wherein the tracked insertion element has openings; and
displaying the rings of the target element representation and rings representing the openings of the insertion element.

17. The assisting method as claimed in claim 13, further comprising:
determining a distance between the target element and the insertion element based on the generated target element representation and the tracked position of the insertion element; and
displaying the determined distance.

18. The assisting method as claimed in claim 13, further comprising:
providing a target element image showing the target element; and
displaying the at least one ring of the target element representation and the at least one ring representing the at least one opening of the insertion element on the target element image.

19. The assisting method as claimed in claim 13, further comprising:
tracking the orientation of the insertion element; and
providing the object image such that an image acquisition direction of the object image depends on the tracked orientation of the insertion element.

20. A non-transitory machine-readable storage medium encoded with instructions for execution by at least one processor for assisting a user in moving an insertion element within an object to a target element, the non-transitory machine-readable storage medium comprising instructions for causing an assisting apparatus as defined in claim 13 to carry out the steps of the assisting method.

* * * * *